US008535719B2

(12) United States Patent
Badylak et al.

(10) Patent No.: US 8,535,719 B2
(45) Date of Patent: Sep. 17, 2013

(54) BIOHYBRID ELASTOMERIC SCAFFOLDS AND METHODS OF USE THEREOF

(75) Inventors: Stephen F. Badylak, Pittsburgh, PA (US); Donald O. Freytes, Pittsburgh, PA (US); Thomas W. Gilbert, Pittsburgh, PA (US); Jianjun Guan, Dublin, OH (US); John Stankus, Campbell, CA (US); William R. Wagner, Wexford, PA (US)

(73) Assignee: University of Pittsburgh - Of the Commonwealth System of Higher Education, Pittsburgh, PA (US)

( * ) Notice: Subject to any disclaimer, the term of this patent is extended or adjusted under 35 U.S.C. 154(b) by 1606 days.

(21) Appl. No.: 11/825,540

(22) Filed: Jul. 6, 2007

(65) Prior Publication Data

US 2008/0268019 A1    Oct. 30, 2008

Related U.S. Application Data

(60) Provisional application No. 60/806,762, filed on Jul. 7, 2006.

(51) Int. Cl.
*A61K 9/70* (2006.01)

(52) U.S. Cl.
USPC ........... 424/484; 424/426; 424/486; 424/551; 424/574; 424/93.7; 514/772.3

(58) Field of Classification Search
None
See application file for complete search history.

(56) References Cited

U.S. PATENT DOCUMENTS

| | | |
|---|---|---|
| 4,902,508 A | 2/1990 | Badylak et al. |
| 4,956,178 A | 9/1990 | Badylak et al. |
| 5,171,262 A | 12/1992 | MacGregor |
| 5,275,826 A | 1/1994 | Badylak et al. |
| 5,281,422 A | 1/1994 | Badylak et al. |
| 5,352,463 A | 10/1994 | Badylak et al. |
| 5,372,821 A | 12/1994 | Badylak et al. |
| 5,516,533 A | 5/1996 | Badylak et al. |
| 5,554,389 A | 9/1996 | Badylak et al. |
| 5,573,784 A | 11/1996 | Badylak et al. |
| 5,645,860 A | 7/1997 | Knapp, Jr. et al. |
| 5,711,969 A | 1/1998 | Patel et al. |
| 5,753,267 A | 5/1998 | Badylak et al. |
| 5,762,966 A | 6/1998 | Knapp, Jr. et al. |
| 5,866,414 A | 2/1999 | Badylak et al. |
| 6,099,567 A | 8/2000 | Badylak et al. |
| 6,485,723 B1 | 11/2002 | Badylak et al. |
| 6,554,857 B1 | 4/2003 | Zilla et al. |
| 6,576,265 B1 | 6/2003 | Spievack |
| 6,579,538 B1 | 6/2003 | Spievack |
| 6,696,270 B2 | 2/2004 | Badylak et al. |
| 6,783,776 B2 | 8/2004 | Spievack |
| 6,793,939 B2 | 9/2004 | Badylak |
| 6,849,273 B2 | 2/2005 | Spievack |
| 6,852,339 B2 | 2/2005 | Spievack |
| 6,861,074 B2 | 3/2005 | Spievack |
| 6,887,495 B2 | 5/2005 | Spievack |
| 6,890,562 B2 | 5/2005 | Spievack |
| 6,890,563 B2 | 5/2005 | Spievack |
| 6,890,564 B2 | 5/2005 | Spievack |
| 6,893,666 B2 | 5/2005 | Spievack |
| 7,235,295 B2 | 6/2007 | Laurencin et al. |
| 7,374,774 B2 | 5/2008 | Bowlin et al. |
| 8,053,559 B2 * | 11/2011 | Nielsen et al. ................ 530/350 |
| 2002/0081732 A1 | 6/2002 | Bowlin et al. |
| 2002/0090725 A1 | 7/2002 | Simpson et al. |
| 2003/0021827 A1 * | 1/2003 | Malaviya et al. ............. 424/424 |
| 2003/0100944 A1 | 5/2003 | Laskin et al. |
| 2007/0014755 A1 | 1/2007 | Beckman et al. |
| 2008/0009830 A1 | 1/2008 | Fujimoto et al. |
| 2008/0096975 A1 | 4/2008 | Guan et al. |
| 2008/0109070 A1 | 5/2008 | Wagner et al. |
| 2008/0260831 A1 | 10/2008 | Badylak et al. |

OTHER PUBLICATIONS

Badylak S, Meurling S, Chen M, Spievack A, Simmons-Byrd A. Resorbable bioscaffold for esophageal repair in a dog model. J Pediatr Surg. Jul. 2000;35(7):1097-103.
Badylak SF, Vorp DA, Spievack AR, Simmons-Byrd A, Hanke J, Freytes DO, Thapa A, Gilbert TW, Nieponice A. Esophageal reconstruction with ECM and muscle tissue in a dog model. J Surg Res. Sep. 2005;128(1):87-97.
Badylak SF. The extracellular matrix as a scaffold for tissue reconstruction. Semin Cell Dev Biol. Oct. 2002;13(5):377-83.
Badylak SF. Xenogeneic extracellular matrix as a scaffold for tissue reconstruction. Transpl Immunol. Apr. 2004;12(3-4):367-77.
Bernacca GM, Mackay TG, Gulbransen MJ, Donn AW, Wheatley DJ. Polyurethane heart valve durability: effects of leaflet thickness and material. Int J Artif Organs. Jun. 1997;20(6):327-31.
Billiar KL, Sacks MS. Biaxial mechanical properties of the natural and glutaraldehyde treated aortic valve cusp—Part I: Experimental results. J Biomech Eng. Feb. 2000;122(1):23-30.
Brightman AO, et al. Time-Lapse Confocal Reflection Microscopy of Collagen Fibrillogenesis and Extracellular Matrix Assembly In Vitro. Biopolymers. Sep. 2000;54(3): 222-34.
Chaudhari BB, Kundu P, Sarkar N. Detection and gradation of oriented texture. Pattern Recogn Lett. 1993;14(2):147-53.
Courtney T, Liao J, Sacks MS, Stankus J, Guan J, Wagner W. Meso- and micromechanics of elastomeric electrospun PEUU scaffolds for cardiovascular tissue engineering. Regenerate World Congress on Tissue Engineering and Regenerative Medicine, Apr. 25-27, 2006, Pittsburgh, PA. Published on CD, Conference Proceedings Regenerate World Congress on Tissue Engineering and Regenerative Medicine, Abstract # 572.

(Continued)

*Primary Examiner* — Allison Ford
(74) *Attorney, Agent, or Firm* — The Webb Law Firm

(57) ABSTRACT

Provided herein is a biohybrid elastomeric scaffold comprising a synthetic polymeric component and a biological polymeric component. The scaffold can be fabricated to have many different forms, non-limiting examples of which include a non-woven fibrous mesh or in a porous composite. Methods of use of the biohybrid elastomeric scaffolds in wound healing and tissue regeneration are also provided.

40 Claims, 5 Drawing Sheets

(56) References Cited

OTHER PUBLICATIONS

Courtney T, Liao J, Sacks MS, Stankus J, Guan J, Wagner W. Micromechanics of electrospun polyester urethane urea scaffolds. Society for Biomaterials 2006 Annual Meeting, Apr. 26-29, 2006, Pittsburgh, PA. Published on CD, Transactions of the 31$^{st}$ Annual Meeting of the Society for Biomaterials, vol. XXIX, Abstract # 163.

Courtney T, Liao J, Stankus J, Guan J, Wagner W, Sacks MS. Micromechanics of electrospun polyester urethane urea scaffolds for soft tissue engineering. Fifth World Congress of Biomechanics, Jul. 29-Aug. 4, 2006, Munich, Germany. Published in Journal of Biomechanics 2006 39(Supp 1): S262.

Courtney T, Sacks MS, Liao J, Stankus J, Guan J, Wagner W. Incorporation of fiber tortuosity effects in a constitutive model for scaffolds. ASME 2006 Summer Bioengineering Conference, Jun. 21-25, 2006, Amelia Island, Florida. Published on CD, Proceedings of the 2006 Summer Bioengineering Conference, Abstract # BIO2005-157686.

Courtney T, Sacks MS, Stankus J, Guan J, Wagner WR Design and analysis of tissue engineering scaffolds that mimic soft tissue mechanical anisotropy. Biomaterials. Jul. 2006;27(19):3631-8. Epub Mar. 20, 2006.

Courtney TD, Sacks MS, Stankus JJ, Guan J, Wagner WR. Analysis and design of novel electrospun PEUU scaffolds for soft tissue engineering. The 8$^{th}$ Annual Meeting of the Tissue Engineering Society International, Oct. 22-25, 2005, Shanghai, P.R. China. Published on CD, Final Program and Abstract Book TESI 2005, Abstract # 193.

Courtney TD, Sacks MS, Stankus JJ, Guan J, Wagner WR. Analysis and design of novel electrospun PEUU scaffolds for soft tissue engineering. ASME 2005 Summer Bioengineering Conference, Vail, CO, Jun. 22-26, 2005. Published on CD, Proceedings of the 2005 Summer Bioengineering Conference Vail Cascade Resort and Spa, Vail, CO; Abstract # b0241329.

Courtney TD, Sacks MS, Stankus JJ, Guan J, Wagner WR. Structural and mechanical characterization of poly(ester urethane) elastomeric scaffolds for cardiovascular soft tissue engineering. Society for Biomaterials 30$^{th}$ Annual Meeting, Memphis, TN, Apr. 27-30, 2005. Published on CD, Transactions of the 30$^{th}$ Annual Meeting.

Courtney TD, et al. Analysis and design of novel electrospun PEUU scaffolds for soft tissue engineering. MRS 2005 Fall, Boston, MA, Nov. 30, 2005, Session L13.1.

Deglau TE, Litwak K, Villanueva FS, Wagner WR. Surface modification of vascular tissue for targeted delivery of endothelial cells and microspheres. Abstract for Biomedical Engineering Society 2000 Annual Fall Meeting, Oct. 12-14, 2000. Ann Biomed Eng. 2000;28(Supplement):S-23.

Grashow JS, Yoganathan AP, Sacks MS. Biaixal stress-stretch behavior of the mitral valve anterior leaflet at physiologic strain rates. Ann Biomed Eng. Feb. 2006;34(2):315-25. Epub Feb. 1, 2006.

Guan J, Fujimoto KL, Sacks MS, Wagner WR. Preparation and characterization of highly porous, biodegradable polyurethane scaffolds for soft tissue applications. Biomaterials. Jun. 2005;26(18):3961-71.

Guan J, Sacks MS, Beckman EJ, Wagner WR. Biodegradable poly(ether ester urethane)urea elastomers based on poly(ether ester) triblock copolymers and putrescine: synthesis, characterization and cytocompatibility. Biomaterials. Jan. 2004;25(1):85-96.

Guan J, Sacks MS, Beckman EJ, Wagner WR. Synthesis, characterization, and cytocompatibility of elastomeric, biodegradable poly-(ester-urethane)ureas based on poly(caprolactone) and putrescine. J Biomed Mater Res. Sep. 5, 2002;61(3):493-503.

Guan J, Wagner WR. Synthesis, characterization and cytocompatibility of polyurethaneurea elastomers with designed elastase sensitivity. Biomacromolecules. Sep.-Oct. 2005;6(5):2833-42.

Karlon WJ, Covell JW, McCulloch AD, Hunter JJ, Omens JH. Automated measurement of myofiber disarray in transgenic mice with ventricular expression of ras. Anat Rec. Dec. 1998;252(4):612-25.

Lee CH, Shin HJ, Cho IH, Kang YM, Kim IA, Park KD, Shin JW. Nanofiber alignment and direction of mechanical strain affect the ECM production of human ACL fibroblast. Biomaterials. Apr. 2005;26(11):1261-70.

Matsuda T, Ihara M, Inoguchi H, Kwon IK, Takamizawa K, Kidoaki S. Mechano-active scaffold design of small-diameter artificial graft made of electrospun segmented polyurethane fabrics. J Biomed Mater Res A. Apr. 1, 2005;73(1):125-31.

Middleton JC, Tipton AJ. Synthetic Biodegradable Polymers as Medical Devices. Medical Plastics and Biomaterials Magazine. Medical Plastics and Biomaterials Magazine. Mar. 1998, p. 30. Available at: http://devicelink.com/mpb/archive/98/03/002.html.

Nedovic VA, Obradovic B, Poncelet D, Goosen MFA, Leskosek-Cukalovic O, Bugarski B. Cell immobiliation by electrostatic droplet generation. Landbauforsch Volk. 2002;(241):11-17.

Radisic M, Yang L, Boublik J, Cohen RJ, Langer R, Freed LE, Vunjak-Novakovic G. Medium perfusion enables engineering of compact and contractile cardiac tissue. Am J Physiol Heart Circ Physiol. Feb. 2004;286(2):H507-16. Epub Oct. 9, 2003.

Riboldi SA, Sampaolesi M, Neuenschwander P, Cossu G, Mantero S. Electrospun degradable polyesterurethane membranes: potential scaffolds for skeletal muscle tissue engineering. Biomaterials. Aug. 2005;26(22):4606-15. Epub Jan. 7, 2005.

Sacks MS. Biaxial mechanical evaluation of planar biological materials. J Elasticity 2000; 61(1-3):199-246.

Santucci RA, Barber TD. Resorbable extracellular matrix grafts in urologic reconstruction. Int Braz J Urol. May-Jun. 2005;31(3):192-203. Review. Erratum in: Int Braz J Urol. Jul.-Aug. 2005;31(4):414.

Stankus JJ, Guan J, Fujimoto K, Wagner WR Microintegrating smooth muscle cells into a biodegradable, elastomeric fiber matrix. Biomaterials. Feb. 2006;27(5):735-44. Epub Aug. 10, 2005.

Stankus JJ, Guan J, Wagner WR. Fabrication of biodegradable elastomeric scaffolds with sub-micron morphologies. J Biomed Mater Res A. Sep. 15, 2004;70(4):603-14.

Stankus JJ, Soletti L, Fujimoto K, Hong Y, Vorp DA, Wagner WR. Fabrication of cell microintegrated blood vessel constructs through electrohydrodynamic atomization. Biomaterials. Jun. 2007;28(17):2738-46. Epub Feb. 20, 2007.

Temple MD, Bashari E, Lu J, Zong WX, Thompson CB, Pinto NJ, Monohar SK, King RCY, MacDiarmid AG. Electrostatic transportation of living cells through air. Abstracts of Papers, 223 ACS National Meeting, Orlando, FL, Apr. 7-11, 2002.

Veazey WS, Anusavice KJ, Moore K. Mammalian cell delivery via aerosol deposition. J Biomed Mater Res B Appl Biomater. Feb. 15, 2005;72(2):334-8.

Venere E. New materials hold promise for human healing applications. Purdue News, Mar. 22, 2001.

Wright Medical Technology. Comparative analysis: GRAFTJACKET™ Periosteum Replacement Scaffold & SIS™ Porcine Small Intestine Submucosa. Copyright in 2002.

Xu CY, Inai R, Kotaki M, Ramakrishna S. Aligned biodegradable nanofibrous structure: a potential scaffold for blood vessel engineering. Biomaterials. Feb. 2004;25(5):877-86.

\* cited by examiner

BIOHYBRID ELASTOMERIC SCAFFOLDS AND METHODS OF USE THEREOF

CROSS-REFERENCE TO RELATED APPLICATIONS

This application claims the benefit under 35 U.S.C. §119(e) to U.S. Provisional Patent Application No. 60/806,762, filed on Jul. 7, 2006, which is incorporated herein by reference in its entirety.

STATEMENT REGARDING FEDERAL FUNDING

The U.S. Government has a paid-up license in this invention and the right in limited circumstances to require the patent owner to license others on reasonable terms as provided for by the terms of Grant No. DAMD17-02-1-0717, awarded by the U.S. Army.

Provided herein are compositions and medical devices, and in particular, biodegradable elastomeric scaffolds comprising both a synthetic component and a biological component. Also provided herein are methods of using the hybrid elastomeric scaffolds for treating wounds and/or promoting tissue regeneration. In one non-limiting use, these biodegradable elastomeric scaffolds can promote tissue regeneration and/or wound healing when applied to open wounds that result from surgery or trauma.

When naturally occurring proteins or chemically-modified naturally occurring proteins are used to make matrices for wound healing and/or tissue regeneration, one faces several potential biological and manufacturing challenges. For example, a naturally occurring material may cause an immunogenic response in a patient, wherein the patient's immune system rejects the matrix. Furthermore, procurement and processing of such naturally occurring materials may be difficult for several reasons. First, the source of the naturally occurring material may be scarce or may only exist in abundance in certain geographic areas. Second, the variability that is intrinsic to natural products may cause unwanted batch variability in both the composition and the mechanical and material properties. These factors, when combined, can make it expensive and/or impracticable to produce matrices based on naturally occurring proteins.

The use of synthetic matrices may be problematic for other reasons. For example, patients can respond to synthetic matrix materials as foreign bodies, leading to inferior wound healing properties and fibrous encapsulation by surrounding host tissues. Moreover, a matrix made of synthetic materials may have different mechanical properties compared to the surrounding tissue, causing undesirable strain including strain at the interface of the matrix and the surrounding tissue.

Thus, there is a need for biodegradable materials that combine the favorable bioreactive and biocompatible properties of naturally-occurring scaffold materials with the reproducible and predictable properties of synthetic scaffold materials. There is also a need for biocompatible and biodegradable materials that are useful for promoting wound and tissue healing that, that possess bioactive components, and that exhibit elastomeric mechanical properties similar to native tissue.

SUMMARY

Provided herein are elastomeric scaffolds that comprise a synthetic polymeric component and a biological polymeric component. The elastomeric scaffolds are biodegradable, porous and biocompatible. Also provided are methods of preparing biodegradable elastomeric scaffolds. Further, methods are provided for promoting wound healing and/or tissue regeneration within a patient. The method comprises implanting a biodegradable elastomeric scaffold at, around or near a site in need of wound healing, tissue remodeling and/or tissue regeneration. In one non-limiting embodiment, the biodegradable elastomeric scaffold is implanted at the site. In another non-limiting embodiment, a biodegradable elastomeric scaffold comprising cells is implanted at the site. For example and without limitation, this method comprises culturing cells in and/or on a biodegradable elastomeric scaffold in vitro and implanting the scaffold at the site. In another non-limiting embodiment, the method comprises placing cells on the biodegradable elastomeric scaffold at the time of surgical implantation. In yet another non-limiting embodiment, the biodegradable elastomeric scaffold comprises bioactive or therapeutic agents, such as, without limitation growth, factors, antibiotics, and anti-inflammatory agents.

Thus provided according to one non-limiting embodiment of the technology disclosed herein is an elastomeric scaffold comprising a synthetic polymeric component and a biological polymeric component, wherein the scaffold is porous, biodegradable, and biocompatible. The synthetic polymeric component may comprise a thermoplastic biodegradable elastomer, and/or the biological polymeric component may comprise an extracellular matrix-derived material. The synthetic polymeric component may comprise one or both of a poly(ester urethane) urea elastomer and a poly(ether ester urethane urea) elastomer. The elastomer may comprise a diamine, such as putrescine or lysine ethyl ester, or a diol. The elastomer may comprise a polycaprolactone or a polycaprolactone diol, such as a triblock copolymer comprising polycaprolactone or a polycaprolactone-b-polyethylene glycol-b-polycaprolactone triblock copolymer. The elastomer may be functionalized with an adhesion-promoting peptide, such as the oligopeptide RGD. In one non-limiting embodiment, the elastomer comprises an isocyanate derivative, a polycaprolactone diol, and a diamine chain extender, which may comprise a ratio of isocyanate derivative:polycaprolactone diol:diamine chain extender of about 2:1:1. In another non-limiting embodiment, the elastomer comprises an isocyanate derivative, a triblock copolymer comprising polycaprolactone, and a diamine chain extender in which the ratio of isocyanate derivative:triblock copolymer:diamine chain extender optionally is about 2:1:1.

According to certain non-limiting embodiments, the biological polymeric component is an extracellular matrix-derived material. The ECM-derived material may be isolated from, for example and without limitation, urinary bladder tissue. In one non-limiting embodiment, the extracellular matrix-derived material comprises epithelial basement membrane and subjacent tunica propria. In another, the extracellular matrix-derived material comprises tunica submucosa. In yet another, extracellular matrix-derived material comprises epithelial basement membrane, subjacent tunica propria and tunica submucosa. In certain non-limiting embodiments, the extracellular matrix-derived material is isolated from small intestinal submucosa or the dermis of the skin.

The elastomeric scaffold may comprise a therapeutic agent. For example and without limitation, the therapeutic agent may be an antimicrobial agent chosen from one or more of: isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate. Optionally, the therapeutic agent may be a growth factor, for example and without limitation, a growth factor chosen from one or more of: basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins, and interferons. The therapeutic agent may be cellular, for example and without limitation one or more of stem cells, precursor stem cells, smooth muscle cells, skeletal myoblasts, myocardial cells, endothelial cells, and genetically modified cells.

The elastomeric scaffold can be prepared by any useful method, such as, without limitation, by casting or electrospinning, including combinations thereof. In a useful electrospinning method, the synthetic polymeric component and a biological polymeric component can be suspended independently or together in a solvent and may therefore be spun together or independently (using, for example two nozzles) to form an elastomeric scaffold. Alternately, or in combination with an electrospinning method, the elastomeric method may be cast into a mold (preform), for example and without limitation by solvent casting or by thermally induced phase separation. In embodiments where casting and electrospinning methods are combined, the polymer compositions used for the casting and for the molding may be the same or different, and may comprised independently biological and synthetic polymer components. Medical devices comprising the an elastomeric scaffold prepared by forming a porous, biodegradable, and biocompatible elastomeric scaffold from a synthetic polymeric component and a biological polymeric component according to any useful method, such as those described herein also are provided.

Methods of promoting wound healing or tissue generation or regeneration in a patient also are provided. The methods comprise, without limitation, implanting an elastomeric scaffold as described herein at or near a site for wound healing or tissue generation or regeneration in the patient. Likewise a method of promoting wound healing or tissue generation or regeneration in a patient is provided comprising contacting an elastomeric scaffold as described herein with cells in vitro (for instance, ex vivo for autologous cells), culturing the cells in vitro so that the cells grow in and/or on the scaffold; and implanting the elastomeric scaffold at or near a site for wound healing or tissue generation or regeneration in the patient. In either method, the elastomeric scaffold may comprise a therapeutic agent as described herein.

BRIEF DESCRIPTION OF THE DRAWINGS

FIG. 5A shows the surface of the scaffold, where the scale bar is 200 µm. FIG. 5B shows the cross-section of the scaffold, where the scale bar is 50 µm.

DETAILED DESCRIPTION

Figure 1:
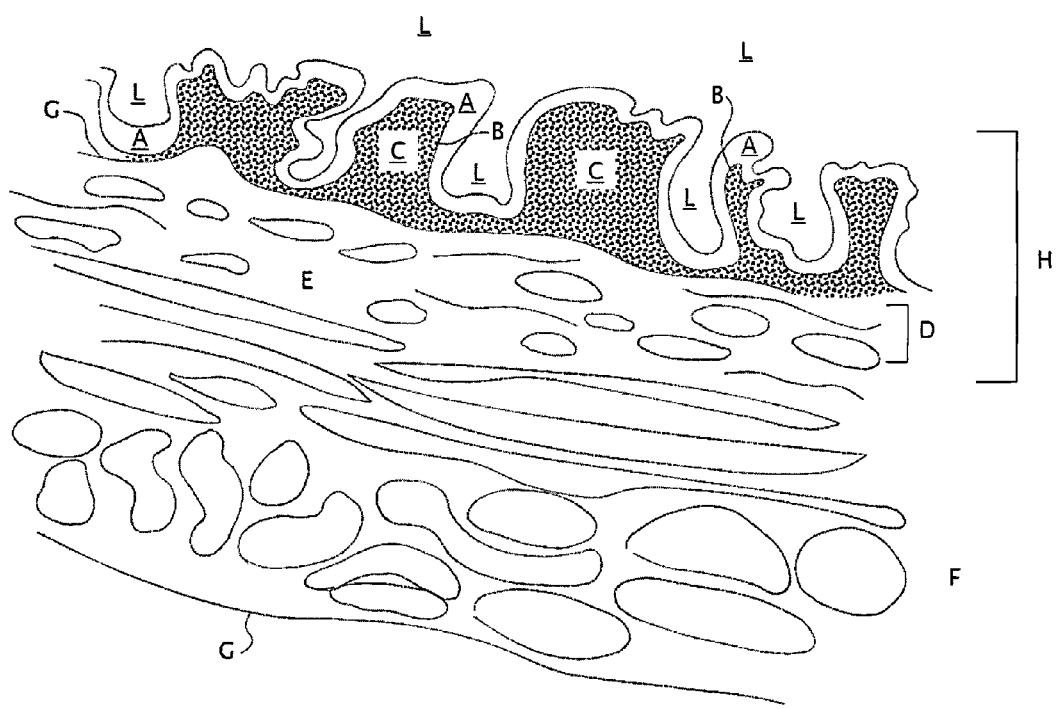
FIG. 1 is a schematic of a cross-sectional view of the wall of the urinary bladder (not drawn to scale). The following structures are shown: epithelial cell layer (A), basement membrane (B), tunica propria (C), muscularis mucosa (D), tunica submucosa (E), tunica muscularis externa (F), tunica serosa (G), tunica mucosa (H), and the lumen of the bladder (L).

Described herein are biodegradable elastomeric scaffolds suitable for use in tissue engineering and regenerative medicine applications. Generally, any elastomeric material that is biocompatible, biodegradable, and has mechanical properties similar to that of native tissue can be used as a biodegradable elastomeric scaffold. In one non-limiting embodiment, the biodegradable elastomeric scaffold comprises a biological polymeric component and a synthetic polymeric component. In another non-limiting embodiment, the scaffold comprises bioactive or therapeutic agents.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

The biodegradable elastomeric scaffold can be used for a large number of medical applications including, but not limited to, wound healing, tissue remodeling, and tissue regeneration. For example and without limitation, the scaffold can be used for wound healing. In one non-limiting embodiment, the scaffold comprises bioactive agents to facilitate tissue healing, tissue remodeling and/or angiogenesis. In another non-limiting embodiment, the scaffold comprises bioactive agents to ward off bacteria and other pathogens. In yet another non-limiting embodiment, the scaffold comprises pores to allow a wound to drain. In another non-limiting embodiment, the scaffold comprises combinations of cells and bioactive agents. In another non-limiting embodiment, combinations of cells and bioactive agents are added to the scaffold before or during implantation at a site in a patient.

As used herein, the term "polymer" refers to both synthetic polymeric components and biological polymeric components. "Biological polymer(s)" are polymers that can be obtained from biological sources, such as, without limitation, mammalian or vertebrate tissue, as in the case of certain extracellular matrix-derived (ECM-derived) compositions. Biological polymers can be modified by additional processing steps. Polymer(s), in general include, for example and without limitation, mono-polymer(s), copolymer(s), polymeric blend(s), block polymer(s), block copolymer(s), cross-linked polymer(s), non-cross-linked polymer(s), linear-, branched-, comb-, star-, and/or dendrite-shaped polymer(s), where polymer(s) can be formed into any useful form, for example and without limitation, a hydrogel, a porous mesh, a fiber, woven mesh, or non-woven mesh, such as, for example and without limitation, as a non-woven mesh formed by electrospinning.

Generally, the polymeric components suitable for the scaffold described herein may be any polymer that is biodegradable and biocompatible. By "biodegradable," it is meant that a polymer, once implanted and placed in contact with bodily fluids and/or tissues, will degrade either partially or completely through chemical, biochemical and/or enzymatic processes. Non-limiting examples of such chemical reactions include acid/base reactions, hydrolysis reactions, and enzymatic cleavage. In certain non-limiting embodiments, the biodegradable polymers may comprise homopolymers, copolymers, and/or polymeric blends comprising, without limitation, one or more of the following monomers: glycolide, lactide, caprolactone, dioxanone, and trimethylene carbonate. In other non-limiting embodiments, the polymer(s) comprise labile chemical moieties, non-limiting examples of which include esters, anhydrides, polyanhydrides, or amides, which can be useful in, for example and without limitation, controlling the degradation rate of the scaffold and/or the release rate of therapeutic agents from the scaffold. Alternatively, the polymer(s) may contain peptides or biomacromolecules as building blocks which are susceptible to chemical reactions once placed in situ. In one non-limiting example, the polymer is a polypeptide comprising the amino acid sequence alanine-alanine-lysine, which confers enzymatic lability to the polymer. In another non-limiting embodiment, the polymer composition may comprise a biomacromolecular component derived from an ECM. For example, the polymer composition may comprise the biomacromolecule collagen so that collagenase, which is present in situ, can degrade the collagen.

The polymer components may be selected so that they degrade in situ on a timescale that is similar to an expected rate of healing of the wound or tissue. Non-limiting examples of useful in situ degradation rates include between one week and one year or increments therebetween for instance, between two weeks and 10 months, and between one month and six month.

The polymeric components used to make the biohybrid elastomeric patch are preferably biocompatible. By "biocompatible," it is meant that a polymer compositions and its normal degradation in vivo products are cytocompatible and are substantially non-toxic and non-carcinogenic in a patient within useful, practical and/or acceptable tolerances. By "cytocompatible," it is meant that the polymer can sustain a population of cells and/or the polymer composition, device, and degradation products, thereof are not cytotoxic and/or carcinogenic within useful, practical and/or acceptable tolerances. For example, the polymer when placed in a human epithelial cell culture does not adversely affect the viability, growth, adhesion, and number of cells. In one non-limiting embodiment, the compositions, and/or devices are "biocompatible" to the extent they are acceptable for use in a human veterinary patient according to applicable regulatory standards in a given jurisdiction. In another example the biocompatible polymer, when implanted in a patient, does not cause a substantial adverse reaction or substantial harm to cells and tissues in the body, for instance, the polymer composition or device does not cause necrosis or an infection resulting in harm to tissues from the implanted scaffold.

The mechanical properties of a biodegradable elastomeric scaffold can be optimized to reduce strain and stress on the native tissue at the site of implantation. In certain non-limiting embodiments, the mechanical properties of the scaffold are optimized similar to or identical to that of native soft tissue, such as fascia, connective tissue, blood vessel, muscle, tendon, fat, etc. In one non-limiting embodiment, the biodegradable elastomeric scaffold comprises a thermoplastic elastomeric polymer. The mechanical properties of the scaffold also may be optimized to be suitable for surgical handling. In one non-limiting embodiment, the scaffold is flexible and can be sutured to the site. In another, the scaffold is foldable and can be delivered to the site by minimally invasive laparoscopic methods.

The physical and/or mechanical properties of the biodegradable elastomeric scaffold can be optimized by any useful method. Variables that can be optimized include without limitation, the extent of physical cross-linking in a network comprising polymeric components, the ratio of polymeric components within the network, the distribution of molecular weight of the polymeric components, and the method of processing the polymers. Polymers are typically semicrystalline and their physical properties and/or morphology are dependant upon a large number of factors, including monomer composition, polydispersity, average molecular weight, cross-linking, and melting/crystallization conditions. For example, flow and/or shear conditions during cooling of a polymer melt are known to affect formation of crystalline structures in the composition. In one non-limiting embodiment, the scaffold comprises a polymeric component that provides strength and durability to the scaffold, yet is elastomeric so that the mechanical properties of the scaffold are similar to the native tissue surrounding the wound or site in need of tissue regeneration.

As described herein, according to certain non-limiting embodiments, one or more of the polymeric components of the biodegradable elastomeric scaffold is elastomeric. In one non-limiting example, the scaffold has physical properties similar to that of soft tissue such as fascia. In certain non-limiting embodiments, the biodegradable elastomeric scaffold comprises highly distensible polymeric components. Examples of suitable polymers include those that have a breaking strain ranging from about 100% to about 900%, including any increments therebetween for example between 200% and 800%, or between 325% and 600%. In other non-limiting embodiments, the breaking strain of the polymer is between 50% and 100% including any increments therebetween. Further, it is often useful to select polymers with tensile strengths of from 10 kPa to 30 MPa, including increments therebetween, such as from 5 MPa to 25 MPa, and between 8 MPa and 20 MPa. In certain non-limiting embodiments, the initial modulus is between 10 kPa to 100 MPa and increments therebetween, such as 10 MPa and 90 MPa, and between 20 MPa and 70 MPa.

In an embodiment in which the scaffold comprises a mixture of polymeric components, and at least one component is elastomeric, the ratio of polymeric components in the mixture can be optimized to obtain an elastomeric mixture of suitable, desirable physical qualities. In one non-limiting embodiment, the mixture has physical properties similar to that of soft tissue such as, without limitation, fascia. In yet another non-limiting embodiment, the mixture comprises at least 90%, 80%, 70%, 60%, 50%, 40%, 30%, 20%, and 10% of the elastomeric polymeric component. For example, according to one embodiment, the mixture comprises 50% of a synthetic polymeric component and 50% of a biological polymeric component, for example and without limitation, the mixture may comprise 50% PEUU by weight and 50% UBM by weight.

In one non-limiting embodiment, the biodegradable elastomeric scaffold comprises a synthetic polymeric component and a biological polymeric component. The synthetic and biological polymeric components may be selected to impart different properties to the biodegradable elastomeric scaffold. For example and without limitation, the synthetic polymeric component may be selected to provide mechanical strength and durability to the scaffold, as well as certain mechanical properties, as described herein. The biological polymeric component may be a material that encourages tissue regeneration and remodeling within the patient, thereby increasing the rate of wound healing.

The synthetic polymeric component can be any useful biocompatible, biodegradable and elastomeric synthetic polymer material. In one non-limiting embodiment, the synthetic polymeric component is a polymer that provides durability as assayed in an accelerated fatigue test as described by Bernacca et al. Int J. Artif. Organs, 20(6): 327-331 (1997). In certain non-limiting embodiments, the synthetic polymeric component comprises a thermoplastic biodegradable elastomer. In another the synthetic polymeric component comprises a phase-separated biodegradable elastomer with degradable soft and/or hard segments. In yet another non-limiting embodiment, the synthetic polymeric component comprises any hydrolytically, chemically, biochemically, and/or proteolytically labile group, non-limiting examples of which include an ester moiety, amide moiety, anhydride moiety, specific peptide sequences, and generic peptide sequences.

In certain non-limiting embodiments, the synthetic polymeric component is a biodegradable elastomeric polyurethane polymer. In one example, the synthetic polymeric component is a linear segmented poly(urethane urea) copolymer, where the copolymer comprises alternating blocks of "soft" and "hard" segments. In one non-limiting embodiment, the soft segment is a polyether or polyester (e.g., polycaprolactone), which may have a glass transition temperature (temperature at which a reversible change occurs in an amorphous material, such as glass or an amorphous polymer, or in amorphous portions of a partially crystalline polymer from, or to, a viscous or rubbery condition to a hard or relatively brittle one) below the use temperature. As used herein, the "use temperature" or like phrases refers to the temperature at which the scaffolding is maintained after implantation, namely the body temperature of a patient, such as 37° C. for a human patient.

In another non-limiting embodiment, the soft segment comprises a multiblock copolymer in which one or more segments are polyester. In one non-limiting embodiment, a pre-polymer is formed by reacting butyl diisocyanate with polycaprolactone diol and then further reacting the pre-polymer with a chain extender, such as butyl diamine and specific peptide sequences (e.g., alanine-alanine-lysine).

The synthetic polymeric component can be prepared by any useful method. According to one non-limiting embodiment, the synthetic polymeric component comprises a biodegradable polymeric portion, an isocyanate derivative, and a diamine chain extender. In one non-limiting example, formation of the polymeric component comprises at least two steps. In the first step, a pre-polymer is formed, for example in one non-limiting embodiment, the pre-polymer comprises an isocyanate-terminated polymer, which is formed by reacting a biodegradable polymer with an isocyanate derivative. In the second step, the pre-polymer can be further reacted to form chemical bonds between pre-polymer molecules. For example, the isocyanate-terminated pre-polymer is reacted with a diamine chain extender, which reacts with the isocyanate moiety to form chemical bonds between pre-polymer molecules. In another non-limiting example, the isocyanate-terminated pre-polymer is reacted with a diol chain extender, which reacts with the isocyanate moiety. As used herein, an "isocyanate derivative" is any molecule or group that is terminated by the moiety —N=C=O. Isocyanate derivates also include, without limitation, monoisocyanates and polyisocyanates, such as diisocyanates and triisocyanates. In one non-limiting embodiment, the isocyanate derivative is 1,4-diisocyanatobutane.

Preparation of polymeric components may include other steps, including, for example and without limitation, catalytic steps, purification steps, and separation steps. The synthetic polymeric component described herein comprises one or more biodegradable, biocompatible polymers. The biodegradable polymers may be, without limitation, homopolymers, copolymers, and/or polymeric blends. The polymer(s) may comprise, without limitation, one or more of the following monomers: glycolide, lactide, caprolactone, dioxanone, and trimethylene carbonate. In one non-limiting embodiment, the polymer comprises a polycaprolactone. In another embodiment, the polymer comprises a polycaprolactone diol. In yet another embodiment, the polymer comprises a triblock copolymer comprising polycaprolactone, poly(ethylene glycol), and polycaprolactone blocks.

As used herein, a "chain extender" is any molecule or group that reacts with an active group, such as, without limitation, an isocyanate derivative, to extend chains of polymers. Non-limiting examples of useful chain extenders are diamines and diols. In one non-limiting embodiment, the chain extender is a diamine that allows for extending the chain of the pre-polymer, such as putrescine (1,4-diaminobutane). In another non-limiting embodiment, the diamine is lysine ethyl ester. In yet another non-limiting embodiment, the diamine is a peptide fragment comprising two or more amino acids, for example and without limitation, the peptide fragment alanine-alanine-lysine, which can be cleaved enzymatically by elastase. In one non-limiting embodiment, the chain extender is a diol that allows for extending the chain of the pre-polymer, such as 1,4-butane diol.

In one non-limiting embodiment, the synthetic polymeric component comprises a biodegradable poly(ester urethane) urea elastomer (PEUU). One non-limiting example of a PEUU is an elastomeric polymer made from polycaprolactone diol (MW 2000) and 1,4-diisocyanatobutane, using a diamine chain extender, such as putrescine. The PEUU copolymer can be prepared by a two-step polymerization process whereby polycaprolactone diol (MW 2000), 1,4-diisocyanatobutane, and diamine are combined in a 2:1:1 molar ratio. In the first step, to form the pre-polymer, a 15 wt % solution of 1,4-diisocyanatobutane in DMSO (dimethyl sulfoxide) is stirred continuously with a 25 wt % solution of polycaprolactone diol in DMSO. Then, stannous octoate is added and the mixture is allowed to react at 75° C. for 3 hours. In the second step, the pre-polymer is reacted with a diamine to extend the chain and to form the polymer. For example and without limitation, the diamine putrescine is added drop-wise while stirring and allowed to react at room temperature for 18 hours. In another non-limiting embodiment, the diamine is lysine ethyl ester, which is dissolved in DMSO with triethylamine, added to the pre-polymer solution, and allowed to react at 75° C. for 18 hours. After the two step polymerization process, the polymer solution is precipitated in distilled water. Then, the wet polymer is immersed in isopropanol for three days to remove any unreacted monomers. Finally, the polymer is dried under vacuum at 50° C. for 24 hours.

In another non-limiting embodiment, the synthetic polymeric component comprises a poly(ether ester urethane) urea elastomer (PEEUU). IN one non-limiting example, the PEEUU is made by reacting polycaprolactone-b-polyethylene glycol-b-polycaprolactone triblock copolymers with 1,4-diisocyanatobutane and putrescine. PEEUU may be obtained, for example and without limitation, by a two-step reaction using a 2:1:1 reactant stoichiometry of 1,4-diisocyanatobutane:triblock copolymer:putrescine. In a further non-limiting example, the triblock polymer is prepared by reacting poly(ethylene glycol) and ε-caprolactone with stannous octoate at 120° C. for 24 hours under a nitrogen environment. The triblock copolymer may be washed with ethyl ether and hexane, then dried in a vacuum oven at 50° C. In the first step to form the pre-polymer, a 15 wt % solution of 1,4-diisocyanatobutane in DMSO is stirred continuously with a 25 wt % solution of triblock copolymer in DMSO. Stannous octoate is then added and the mixture is allowed to react at 75° C. for 3 hours. In the second step, putrescine is added drop-wise under stirring to the pre-polymer solution and allowed to react at room temperature for 18 hours. The PEEUU polymer solution is then precipitated with distilled water. The wet polymer is immersed in isopropanol for 3 days to remove unreacted monomer and dried under vacuum at 50° C. for 24 hours.

The biological polymeric component is useful for promoting cell growth on the elastomeric scaffold, extracting appropriate host cells for construction, remodeling, and/or enhancement of biocompatibility. In one non-limiting embodiment, the biological polymeric component comprises and includes an extracellular matrix-derived material. As used herein, the terms "extracellular matrix" and "ECM" refer to a complex mixture of structural and functional biomolecules and/or biomacromolecules including, but not limited to, structural proteins, specialized proteins, proteoglycans, glycosaminoglycans, and growth factors that surround and support cells within mammalian tissues.

Generally, any type of extracellular matrix (ECM) can be used to prepare the biological, ECM-derived polymeric component of the biodegradable elastomeric scaffold (for example and without limitation, see U.S. Pat. Nos. 4,902,508; 4,956,178; 5,281,422; 5,352,463; 5,372,821; 5,554,389; 5,573,784; 5,645,860; 5,771,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; and 6,893,666; each of which is incorporated by reference in its entirety). By "ECM-derived material" it is meant a composition that is prepared from a natural ECM or from an in vitro source wherein the ECM is produced by cultured cells and comprises one or more polymeric components (constituents) of native ECM.

According to one non-limiting example of the ECM-derived material, ECM is isolated from a vertebrate animal, for example, from a warm blooded mammalian vertebrate animal including, but not limited to, human, monkey, pig, cow, sheep, etc. The ECM may be derived from any organ or tissue, including without limitation, urinary bladder, intestine, liver, heart, esophagus, spleen, stomach and dermis. The ECM can comprise any portion or tissue obtained from an organ, including, for example and without limitation, submucosa, epithelial basement membrane, tunica propria, etc. In one non-limiting embodiment, the ECM is isolated from urinary bladder, which may or may not include the basement membrane. In another non-limiting embodiment, the ECM includes at least a portion of the basement membrane. In certain non-limiting embodiments, the material that serves as the biological component of the scaffold consists primarily (e.g., greater than 70%, 80%, or 90%) of ECM. In another non-limiting embodiment, the biodegradable elastomeric scaffold may contain at least 50% ECM, at least 60% ECM, at least 70% ECM, and at least 80% ECM. In yet another non-limiting embodiment, the biodegradable elastomeric scaffold comprises at least 10% ECM. The ECM material may or may not retain some of the cellular elements that comprised the original tissue such as capillary endothelial cells or fibrocytes. The type of ECM used in the scaffold can vary depending on the intended cell types to be recruited during wound healing or tissue regeneration, the native tissue architecture of the tissue organ to be replaced, the availability of the tissue source of ECM, or other factors that affect the quality of the final scaffold and the possibility of manufacturing the scaffold. For example and without limitation, the ECM may contain both a basement membrane surface and a non-basement membrane surface, which would be useful for promoting the reconstruction of tissue such as the urinary bladder, esophagus, or blood vessel all of which have a basement membrane and non-basement membrane component.

In one non-limiting embodiment, the ECM is harvested from porcine urinary bladders (also known as urinary bladder matrix or UBM). Briefly, the ECM is prepared by removing the urinary bladder tissue from a pig and trimming residual external connective tissues, including adipose tissue. All residual urine is removed by repeated washes with tap water. The tissue is delaminated by first soaking the tissue in a deepithelializing solution, for example and without limitation, hypertonic saline (e.g. 1.0 N saline), for periods of time ranging from ten minutes to four hours. Exposure to hypertonic saline solution removes the epithelial cells from the underlying basement membrane. Optionally, a calcium chelating agent may be added to the saline solution. The tissue remaining after the initial delamination procedure includes the epithelial basement membrane and tissue layers abluminal to the epithelial basement membrane. This tissue is next subjected to further treatment to remove most of the abluminal tissues but maintain the epithelial basement membrane and the tunica propria. The outer serosal, adventitial, tunica muscularis mucosa, tunica submucosa and most of the muscularis mucosa are removed from the remaining deepithelialized tissue by mechanical abrasion or by a combination of enzymatic treatment (e.g., using trypsin or collagenase) followed by hydration, and abrasion. Mechanical removal of these tissues is accomplished by removal of mesenteric tissues with, for example and without limitation, Adson-Brown forceps and Metzenbaum scissors and wiping away the tunica muscularis and tunica submucosa using a longitudinal wiping motion with a scalpel handle or other rigid object wrapped in moistened gauze. Automated robotic procedures involving cutting blades, lasers and other methods of tissue separation are also contemplated. After these tissues are removed, the resulting ECM consists mainly of epithelial basement membrane and subjacent tunica propria (layers B and C of FIG. 1).

In another embodiment, the ECM is prepared by abrading porcine bladder tissue to remove the outer layers including both the tunica serosa and the tunica muscularis (layers G and F in FIG. 1) using a longitudinal wiping motion with a scalpel handle and moistened gauze. Following eversion of the tissue segment, the luminal portion of the tunica mucosa (layer H in FIG. 1) is delaminated from the underlying tissue using the same wiping motion. Care is taken to prevent perforation of the submucosa (layer E of FIG. 1). After these tissues are removed, the resulting ECM consists mainly of the tunica submucosa (layer E of FIG. 1).

The ECM can be sterilized by any of a number of standard methods without loss of function. For example and without limitation, the material can be sterilized by propylene oxide or ethylene oxide treatment, gamma irradiation treatment (0.05 to 4 mRad), gas plasma sterilization, peracetic acid sterilization, or electron beam treatment. Treatment with glutaraldehyde results in sterilization as well as increased cross-linking of the ECM. This treatment substantially alters the material such that it is slowly resorbed or not resorbed at all and incites a different type of host remodeling, which more closely resembles scar tissue formation or encapsulation rather than constructive remodeling. If desired, cross-linking of the protein material within the ECM can also be induced with, for example and without limitation, carbodiimide isocyanate treatments, dehydrothermal methods, and photooxidation methods. In one non-limiting embodiment, the ECM is disinfected by immersion in 0.1% (v/v) peracetic acid, 4% (v/v) ethanol, and 96% (v/v) sterile water for two hours. The ECM material is then washed twice for 15 minutes with PBS (pH=7.4) and twice for 15 minutes with deionized water. The ECM-derived material may be further processed by optionally drying, desiccation, lyophilization, freeze drying, glassification. The ECM-derived material optionally can be further digested, for example and without limitation by hydration (if dried), acidification, enzymatic digests with, for example and without limitation, trypsin or pepsin and neutralization.

Commercially available ECM preparations can also be used as the biological polymeric component of the scaffold. In one non-limiting embodiment, the ECM is derived from small intestinal submucosa or SIS. Commercially available preparations include, but are not limited to, Surgisis™, Surgisis-ES™, Stratasis™, and Stratasis-ES™ (Cook Urological Inc.; Indianapolis, Ind.) and GraftPatch™ (Organogenesis Inc.; Canton Mass.). In another non-limiting embodiment, the ECM is derived from dermis. Commercially available preparations include, but are not limited to Pelvicol™ (sold as Permacol™ in Europe; Bard, Covington, Ga.), Repliform™ (Microvasive; Boston, Mass.) and Alloderm™ (LifeCell; Branchburg, N.J.). In another embodiment, the ECM is derived from urinary bladder. Commercially available preparations include, but are not limited to UBM (Acell Corporation; Jessup, Md.).

In general, the biodegradable elastomeric scaffold described herein may be made using any useful method, including one to the many common processes known in the polymer and textile arts. The biodegradable elastomeric scaffold may take many different forms. In certain non-limiting embodiments, the biodegradable elastomeric scaffold comprises a thin, flexible fabric that can be sewn directly on to the site to be treated. In another non-limiting embodiment, the scaffold comprises a non-woven mat that can be saturated in place at the site of implantation or affixed using a medically acceptable adhesive. In one non-limiting embodiment, the scaffold is substantially planar (having much greater dimension in two dimensions and a substantially smaller dimension in a third, comparable to bandages, gauze, and other substantially flexible, flat items). In another non-limiting embodiment, the biodegradable elastomeric scaffold comprises a non-woven fibrous article formed by electrospinning a suspension containing the synthetic polymeric component and the biological polymeric component. In yet another non-limiting embodiment, the biodegradable elastomeric scaffold comprises a porous composite formed by thermally induced phase separation.

The biodegradable elastomeric scaffold can also have three-dimensional shapes useful for treating wounds and tissue deficiencies, such as plugs, rings, wires, cylinders, tubes, or disks. A useful range of thickness for the biodegradable elastomeric scaffold is between from about 10 μm (micrometers or microns (μ)) to about 3.5 cm, including increments therebetween, including, without limitation from about 10 μm to about 50 μm, 50 μm to 3.5 cm, 100 μm to 3.0 cm, and between 300 μm and 2.5 cm.

In certain non-limiting embodiments, the formation and initial processing of the synthetic polymeric component and the biological polymeric component are separate. For example, the synthesis and dissolution of the synthetic polymeric component may involve solvents that would adversely affect the desirable biological properties of the biological polymeric component. By performing the synthesis and initial processing of the synthetic polymeric component separately from the corresponding synthesis and initial processing steps of the biological polymeric component, it is possible to substantially protect the biological polymeric component against degradation that it would otherwise face when exposed to the solvents used in the synthesis and processing the synthetic polymeric component. In certain non-limiting embodiments, the synthetic polymeric component and biological polymeric component are dispersed in different solvents and subsequently combined (e.g., by combining solvent streams) to form the elastomeric scaffold.

In one non-limiting embodiment, the biodegradable elastomeric scaffold is made by using solvent casting to form a film. This method involves dissolving the polymer in a suitable organic solvent and casting the solution in a mold. For example and without limitation, a 3 wt % solution of the polymer in N,N-dimethylformamide (DMF) is cast into a polytetrafluoroethylene coated dish. Then, DMF typically is evaporated at room temperature and the film is further dried under vacuum.

The biodegradable elastomeric scaffolds may be porous. Porosity may be accomplished by a variety of methods. Although the biodegradable elastomeric scaffolds may be porous or non-porous, it is often advantageous to use a process that produces a porous elastomeric scaffold. Non-limiting examples of such processes include solvent casting/salt leaching, electrospinning, and thermally induced phase separation. In other examples, porosity may be accomplished by creating a mesh of fibers, such as by the aforementioned electrospinning or by ant suitable method of producing a woven or non-woven fiber matrix. As used herein, the term "porosity" refers to a ratio between a volume of all the pores within the polymer composition and a volume of the whole polymer composition. For instance, a polymer composition with a porosity of 85% would have 85% of its volume containing pores and 15% of its volume containing the polymer. In certain non-limiting embodiments, the porosity of the scaffold is at least 60%, 65%, 70%, 75%, 80%, 85%, or 90%, or increments therebetween. In another non-limiting embodiment, the average pore size of the scaffold is between 0.1 and 300 microns, including increments therebetween. For example and without limitation, a biodegradable elastomeric scaffold that acts as a barrier to bacteria and other pathogens may have an average pore size of less than 0.5 microns or less than 0.2 microns. When the scaffold is to be manufactured by electrospinning, it is often advantageous to adjust the pore size or degree of porosity by varying the polymer concentration of the electrospinning solution or by varying the spinning distance from the nozzle to the target. For example and without limitation, the average pore size may be increased by increasing the amount of polymeric components within the suspension used for electrospinning, which results in larger fiber diameters and therefore larger pore sizes. In another non-limiting example, the average pore size can be increased by increasing spinning distance from the nozzle to the target, which results in less adherence between fibers and a looser matrix.

The composition of the polymer suspension can affect the physical properties of the resultant elastomeric scaffold. In the biohybrid scaffolding described herein, the synthetic polymeric component typically, but not exclusively, is more mechanically robust than the biological polymeric component. Thus, to produce an elastomeric scaffold with increased mechanical strength, it may be advantageous to increase the amount of synthetic polymeric component relative to the biological polymeric component. On the other hand, to promote rapid healing, it may be advantageous to increase the relative amount of the biological polymeric component if cells grow more readily on the biological polymeric component. In one non-limiting embodiment, PEUU and UBM are mixed at a 1:1 ratio (w/w) and then dissolved at 6 wt % in hexafluoroisopropanol. Nevertheless, the relative ration of biologic and synthetic polymer components may vary greatly from, for example and without limitation, 10,000:1 to 1:10,000 and increments therebetween, including from 1,000:1 to 1:1,000; from 100:1 to 1:100, from 10:1 to 1:10, such as 0.01 wt %, 0.1 wt %, 1 wt %, 2 wt %, 5 wt %, 10 wt %, 25 wt %, 33 wt %, 50 wt %, 67 wt %, 75 wt %, 90 wt %, 95 wt %, 98 wt %, 99 wt %, 99.9 wt % and 99.99 wt % of synthetic polymer as a percentage of the total weight of the synthetic and biological polymeric components.

In certain non-limiting embodiments, the biodegradable elastomeric scaffold is made by using solvent casting and salt leaching. This method involves dissolving the polymeric components that constitute the scaffold into a suitable organic solvent and then casting the solution into a mold containing small particles of predetermined size (known as porogens). Examples of suitable porogens include inorganic salts, crystals of saccharose, gelatin spheres or paraffin spheres. By adjusting the porogen size and/or the ratio of porogen to solvent, the porosity of the final elastomeric scaffold may be adjusted. After casting, the solvent is evaporated, and the resulting polymer composition is immersed into a second solvent that dissolves the porogen, but not the polymer, to produce a porous, sheet-like structure.

In other non-limiting embodiments, electrospinning is used to fabricate the elastomeric scaffold. The process of electrospinning involves placing a polymer-containing fluid (for example, a polymer solution, a polymer suspension, or a polymer melt) in a reservoir equipped with a small orifice, such as a needle or pipette tip and a metering pump. One electrode of a high voltage source is also placed in electrical contact with the polymer-containing fluid or orifice, while the other electrode is placed in electrical contact with a target (typically a collector screen or rotating mandrel). During electrospinning, the polymer-containing fluid is charged by the application of high voltage to the solution or orifice (for example, about 3-15 kV) and then forced through the small orifice by the metering pump that provides steady flow. While the polymer-containing fluid at the orifice normally would have a hemispherical shape due to surface tension, the application of the high voltage causes the otherwise hemispherically shaped polymer-containing fluid at the orifice to elongate to form a conical shape known as a Taylor cone. With sufficiently high voltage applied to the polymer-containing fluid and/or orifice, the repulsive electrostatic force of the charged polymer-containing fluid overcomes the surface tension and a charged jet of fluid is ejected from the tip of the Taylor cone and accelerated towards the target, which typically is biased between −2 to −10 kV. Optionally, a focusing ring with an applied bias (for example, 1-10 kV) can be used to direct the trajectory of the charged jet of polymer-containing fluid. As the charged jet of fluid travels towards the biased target, it undergoes a complicated whipping and bending motion. If the fluid is a polymer solution or suspension, the solvent typically evaporates during mid-flight, leaving behind a polymer fiber on the biased target. If the fluid is a polymer melt, the molten polymer cools and solidifies in mid-flight and is collected as a polymer fiber on the biased target. As the polymer fibers accumulate on the biased target, a non-woven, porous mesh is formed on the biased target.

The properties of the electrospun elastomeric scaffolds can be tailored by varying the electrospinning conditions. For example, when the biased target is relatively close to the orifice, the resulting electrospun mesh tends to contain unevenly thick fibers, such that some areas of the fiber have a "bead-like" appearance. However, as the biased target is moved further away from the orifice, the fibers of the non-woven mesh tend to be more uniform in thickness. Moreover, the biased target can be moved relative to the orifice. In certain non-limiting embodiments, the biased target is moved back and forth in a regular, periodic fashion, such that fibers of the non-woven mesh are substantially parallel to each other. When this is the case, the resulting non-woven mesh may have a higher resistance to strain in the direction parallel to the fibers, compared to the direction perpendicular to the fibers. In other non-limiting embodiments, the biased target is moved randomly relative to the orifice, so that the resistance to strain in the plane of the non-woven mesh is isotropic. The target can also be a rotating mandrel. In this case, the properties of the non-woven mesh may be changed by varying the speed of rotation. The properties of the electrospun elastomeric scaffold may also be varied by changing the magnitude of the voltages applied to the electrospinning system. In one non-limiting embodiment, the electrospinning apparatus includes an orifice biased to 12 kV, a target biased to −7 kV, and a focusing ring biased to 3 kV. Moreover, a useful orifice diameter is 0.047" (I.D.) and a useful target distance is about 23 cm. Other electrospinning conditions that can be varied include, for example and without limitation, the feed rate of the polymer solutions, the solution concentrations, and the polymer molecular weight.

In one non-limiting embodiment, the biodegradable elastomeric scaffold is produced by electrospinning a polymer suspension comprising a synthetic polymeric component and a biological polymeric component. In another non-limiting embodiment, the biodegradable elastomeric scaffold is produced by electrospinning a polymer suspension comprising a synthetic polymeric component from one nozzle and a polymer suspension comprising a biological polymeric component from another nozzle. Non-limiting examples of useful range of high-voltage to be applied to the polymer suspension is from 0.5 to 30 kV, from 5 to 25 kV, and from 10 to 15 kV.

In an electrospinning method, the concentration of the synthetic and biological polymeric components in the polymer suspension used to prepare the scaffolding can also be varied to modify the physical properties of the biodegradable elastomeric scaffold. For example and without limitation, when the synthetic and biological polymeric components are present at relatively low concentrations, the resulting fibers of the electrospun non-woven mesh typically will have a smaller diameter than when these components are present at relatively high concentrations. Useful range of concentrations for the polymeric components include, without limitation, from 1 wt % to 15 wt % including increments therebetween, for example from 4 wt % to 10 wt %, and from 6 wt % to 8 wt %.

In another non-limiting embodiment, thermally induced phase separation (TIPS) is used to fabricate the biodegradable elastomeric scaffold. This method involves dispersing the polymeric components in a solvent (for example and without limitation, DMSO—dimethyl sulfoxide) and then casted, for example by injecting or otherwise placing the composition into a mold. The mold can have any useful shape, such as a sheet or net. In a typical TIPS fabrication process, a pre-formed mold is cooled to low temperature (for example and without limitation −80° C.), which causes the polymeric components to separate out of the solvent. The mold is then transferred to ethanol to extract the DMSO. In one non-limiting embodiment, PEUU (10% w/v) is initially dissolved in DMSO at 80° C., injected into a mold, cooled over 3 hours to −80° C., kept in ethanol at 4° C. for seven days, and freeze dried for 48 hours.

Fabrication and modification of the biodegradable elastomeric scaffold can comprise multiple steps using multiple techniques using polymer compositions that are the same or different. In one non-limiting example, TIPS is used to fabricate the biodegradable elastomeric scaffold and electrospinning is used to form a fiber coating onto or around the scaffold. In another non-limiting example, solvent casting/salt leaching is used to fabricate the biodegradable elastomeric scaffold and electrospinning is used to form a fiber coating onto or around the scaffold. The electrospinning solution can contain one or more of any polymeric components, including synthetic polymeric components, biological polymeric components, or mixtures of both. The fiber coating formed by electrospinning can be coated onto or around the entire scaffold or portions of the scaffold.

After fabricating the biodegradable elastomeric scaffold, the planar or three-dimensional surface of the scaffold may be functionally modified (functionalized) for any purpose, such as, without limitation, to promote cellular adhesion and migration onto and/or into the scaffold. In one non-limiting example, the surface is first treated to introduce a reactive group on the surface by any useful process, such as one of the many processes known in the art. Second, the activated surface is reacted with an adhesion-promoting peptide or group. The reactive group on the surface can be, for example and without limitation, a hydroxyl group or an amine group. In one embodiment, radio-frequency glow discharge is used to produce plasma containing ammonia gas and amine groups are introduced to the surface by treatment with the plasma. In another embodiment, radio-frequency glow discharge is used to introduce hydroxyl groups to the surface by treatment with plasma.

The activated surface can be modified with an adhesion-promoting oligopeptide to promote cellular ingrowth into and/or onto the scaffold. Non-limiting examples of adhesion-promoting oligopeptides include: RGD or RGDS (SEQ ID NO.: 1), a recognition site for fibronectin, vitronectin, fibrinogen, von Willebrand factor, and collagen; LDV, REDV (SEQ ID NO.: 2), PHSRN (SEQ ID NO.: 3), and KNEED (SEQ ID NO.: 4), which are recognition sites for fibronectin; YIGSR (SEQ ID NO.: 5) and IKVAV (SEQ ID NO.: 6), which are recognition sites for laminin; and DGEA (SEQ ID NO.: 7), a recognition site for collagen.

In one specific non-limiting embodiment, the patch is functionalized to present the peptide RGDS (SEQ ID NO.: 1) on its surface. First, the surface is treated with radio-frequency glow discharge containing ammonia gas to introduce amine groups. Ammonia-containing gas is generated by connecting a flask containing ammonia hydroxide (30 wt % solution) to the glow discharge reactor and maintaining pressure at $3 \times 10^{-3}$ Torr. The surface is further treated with 1,4-diisocyanatobutane to provide a reactive isocyanate group. Next, RGDS (SEQ ID NO.: 1) is attached to the activated surface. The activated surface is immersed in a solution of 20 µg/mL RGDS (SEQ ID NO.: 1) in PBS for 10 hours and then rinsed with PBS.

One or more of therapeutic agents can be introduced into the biodegradable elastomeric scaffold by any useful method, such as, without limitation absorption, adsorption, deposition, admixture with a polymer composition used to manufacture the scaffold and linkage of the agent to a component of the scaffold. In one non-limiting example, the therapeutic agent is introduced into a backbone of a polymer used in the scaffold. By adding the therapeutic agent to the elastomeric polymer itself, the rate of release of the therapeutic agent may be controlled by the rate of polymer degradation. In another non-limiting example, the therapeutic agent is introduced when the scaffold is being made. For instance, during a solvent casting or TIPS process, the therapeutic agent can be added to the solvent with the polymer in the pre-formed mold. During an electrospinning process, the therapeutic agent can be electrosprayed onto the polymer being spun. In yet another non-limiting example, the therapeutic agent is introduced into the scaffold after the patch is made. For instance, the scaffold may be "loaded" with therapeutic agent(s) by using static methods. For instance, the scaffold can be immersed into a solution containing the therapeutic agent permitting the agent to absorb into and/or adsorb onto the scaffold. The scaffold may also be loaded by using dynamic methods. For instance, a solution containing the therapeutic agent can be perfused or electrodeposited into the scaffold. In another instance, a therapeutic agent can be added to the biodegradable elastomeric scaffold before it is implanted in the patient.

Therapeutic agents within the biodegradable elastomeric scaffold can be used in any number of ways. In one non-limiting embodiment, a therapeutic agent is released from the scaffold. For example and without limitation, anti-inflammatory drugs are released from the scaffold to decrease an immune response. In another non-limiting embodiment, a therapeutic agent is intended to substantially remain within the scaffold. For example and without limitation, chemoattractants are maintained within the scaffold to promote cellular migration and/or cellular infiltration into the scaffold.

In one non-limiting embodiment, the biodegradable elastomeric scaffolds release therapeutic agents when the polymeric components degrade within the patient's body. For example and without limitation, the individual building blocks of the polymers may be chosen such that the building blocks themselves provide a therapeutic benefit when released in situ through the degradation process. In one non-limiting embodiment, one of the polymer building blocks is putrescine, which has been implicated as a substance that causes cell growth and cell differentiation.

In another non-limiting embodiment, at least one therapeutic agent is added to the biodegradable elastomeric scaffold before it is implanted in the patient. Generally, the therapeutic agents include any substance that can be coated on, embedded into, absorbed into, adsorbed to, or otherwise attached to or incorporated onto or into the biodegradable elastomeric scaffold that would provide a therapeutic benefit to a patient. Non-limiting examples of such therapeutic agents include antimicrobial agents, growth factors, emollients, retinoids, and topical steroids. Each therapeutic agent may be used alone or in combination with other therapeutic agents. For example and without limitation, a biodegradable elastomeric scaffold comprising neurotrophic agents or cells that express neurotrophic agents may be applied to a wound that is near a critical region of the central nervous system, such as the spine. Alternatively, the therapeutic agent may be blended with the polymer while the polymer is being processed. For example, the therapeutic agent may be dissolved in a solvent (e.g., DMSO) and added to the polymer blend during processing. In another embodiment, the therapeutic agent is mixed with a carrier polymer (e.g., polylactic-glycolic acid microparticles) which is subsequently processed with an elastomeric polymer. By blending the therapeutic agent with a carrier polymer or elastomeric polymer itself, the rate of release of the therapeutic agent may be controlled by the rate of polymer degradation.

In certain non-limiting embodiments, the therapeutic agent is a growth factor, such as a neurotrophic or angiogenic factor, which optionally may be prepared using recombinant techniques. Non-limiting examples of growth factors include basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins, and interferons. Commercial preparations of various growth factors, including neurotrophic and angiogenic factors, are available from R & D Systems, Minneapolis, Minn.; Biovision, Inc, Mountain View, Calif.; ProSpec-Tany TechnoGene Ltd., Rehovot, Israel; and Cell Sciences®, Canton, Mass.

In certain non-limiting embodiments, the therapeutic agent is an antimicrobial agent, such as, without limitation, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate.

In certain non-limiting embodiments, the therapeutic agent is an anti-inflammatory agent, such as, without limitation, an NSAID, such as salicylic acid, indomethacin, sodium indomethacin trihydrate, salicylamide, naproxen, colchicine, fenoprofen, sulindac, diflunisal, diclofenac, indoprofen, sodium salicylamide; an anti-inflammatory cytokine; an anti-inflammatory protein; a steroidal anti-inflammatory agent; or an anti-clotting agents, such as heparin. Other drugs that may promote wound healing and/or tissue regeneration may also be included.

In certain non-limiting embodiments, the therapeutic agent comprises cells that are added to the biodegradable elastomeric scaffold before or at the time of implantation. In such embodiments, it is often advantageous to use a porous biodegradable elastomeric scaffold, so that the cells may be incorporated into the porous structure of the scaffold (a condition referred to as "microintegration"). In this way, most of the cells will have a tendency to be trapped or otherwise contained within the porous structure of the scaffold. The cells that are microintegrated may remain after the biodegradable elastomeric scaffold has fully disintegrated within the patient. However, the microintegrated cells may also be merely cells that act as precursors to the final tissue that is formed when the biodegradable elastomeric scaffold has fully degraded.

Cells may be autologous (obtained from the patient to receive the scaffold), from an allogeneic or xenogeneic source or from any useful cell line, such as, without limitation, stem cells that are capable of cellular growth, remodeling, and/or differentiation. By way of example only, the cells that may be incorporated onto or into the biodegradable scaffold include stem cells, precursor cells, smooth muscle cells, skeletal myoblasts, myocardial cells, endothelial cells, and genetically modified cells. Various commercially available cell lines include Clonetics® Primary Cell Systems (Lonza Group, Inc., Switzerland), ATCC.

Cells may be microintegrated with the biodegradable elastomeric scaffold using a variety of methods. For example and without limitation, the elastomeric scaffold may be submersed in an appropriate growth medium for the cells of interest, and then exposed to the cells. The cells are allowed to proliferate on the surface and interstices of the elastomeric scaffold. The elastomeric scaffold is then removed from the growth medium, washed if necessary, and implanted. Alternatively, the cells maybe placed in a suitable buffer or liquid growth medium and drawn through the scaffold by using vacuum filtration. In another non-limiting embodiment, the cells of interest are dissolved into an appropriate solution (e.g., a growth medium or buffer) and then sprayed onto a biodegradable elastomeric scaffold while the scaffold is being formed by electrospinning. In yet another non-limiting embodiment, the cells are placed in a solution that is biased and then electrosprayed onto the biodegradable elastomeric scaffold while it is being electrospun. By way of example only, the cells that may be incorporated on or into the biodegradable scaffold include stem cells, precursor cells, smooth muscle cells, skeletal myoblasts, myocardial cells, endothelial cells, and genetically modified cells.

In one non-limiting embodiment, the genetically modified cells are capable of expressing a therapeutic substance, such as a growth factor. Cells can be modified by any useful method in the art. For example and without limitation, the therapeutic agent is a growth factor that is released by cells transfected with cDNA encoding for the growth factor. Therapeutics agents that can be released from cells include, without limitation, a neurotrophic factor, such as nerve growth factor, brain-derived neurotrophic factor, neurotrophin-3, neurotrophin-4, neurotrophin-5, and ciliary neurotrophic factor; a growth factor, such as basic fibroblast growth factor (bFGF), acidic fibroblast growth factor (aFGF), vascular endothelial growth factor (VEGF), hepatocyte growth factor (HGF), insulin-like growth factors (IGF), platelet derived growth factor (PDGF), transforming growth factor-beta (TGF-β), pleiotrophin protein (neurite growth-promoting factor 1), and midkine protein (neurite growth-promoting factor 2); an anti-inflammatory cytokine; and an anti-inflammatory protein. The cells may be autologous, allogeneic, etc.

In addition to providing biodegradable elastomeric scaffolds as described above, methods of using such biohybrid elastomeric scaffolds are encompassed herein. Generally, a biodegradable elastomeric scaffold can be implanted by using any suitable medical procedure that facilitates use of the scaffold to provide a therapeutic benefit. As used herein, the terms "implanted" and "implantation" and like terms refer to an act of delivering a biodegradable elastomeric scaffold to a site within the patient and of affixing the scaffold to the site. The site of implantation in a patient typically is "at or near a site for wound healing or tissue generation or regeneration in the patient," meaning the scaffold-containing device is implanted in, on, onto, adjacent to or in proximity to a desired site of delivery to facilitate healing and/or tissue generation or regeneration to repair an injury or defect in the patient and/or to achieve a desired effect in the patient, such as wound drainage. The delivery method may also include minimally invasive methods such as by catheter based technology or by needle injection. The patient may be human or animal. The scaffold may be delivered by any surgical procedure, including minimally invasive techniques, such as laparoscopic surgery, as well as invasive techniques such as thoracic surgery and fasciotomy. In certain non-limiting embodiments, the elastomeric scaffolds are used as surgical fabrics. For example and without limitation, the elastomeric scaffolds can be implanted in a patient during laparoscopic procedures to repair or to reinforce fasciae that have been damaged or weakened. The elastomeric scaffolds can also be used to re-join organs that have been separated as a result of surgery, to treat hernias, and to promote the healing of surgical incisions. The biodegradable elastomeric scaffold may be implanted alone or implanted in conjunction with surgical fasteners, such as sutures, staples, adhesives, screws, pins, and the like. Additionally, biocompatible adhesives, such as, without limitation, fibrin-based glue) may be used to fasten the elastomeric scaffolds as well.

In other non-limiting embodiments, the biodegradable elastomeric scaffolds may be used to promote healing of deep tissue wounds, such as puncture wounds, bullet wounds, or wounds that result from the surgical removal of a substantial amount of tissue, such as in debridement procedures or removal of tumors. In yet another non-limiting embodiment, the scaffold can be in the form of a powder or fine particles (for example, formed by shredding a non-woven mesh formed by electrospinning or TIPS), and is packed directly into the wound to provide a matrix on which the patient's cells may grow. In these situations, it may be advantageous to derivatize the elastomeric scaffold with therapeutic agents, such as antibiotics or growth factors, prior to insertion into the wound.

Other uses of the elastomeric scaffolds include myocardial replacement, and blood vessel (especially arterial) replacement.

EXAMPLES

Example 1

Synthesis of Poly(Ester Urethane) Urea Elastomer (PEUU)

PEUU synthesis was carried out in a 250 mL round bottom flask under nitrogen with reactant stoichiometry of 2:1:1 (1,4-diisocyanatobutane:polycaprolactone diol:putrescine). 15 wt % 1,4-diisocyanatobutane in DMSO was continuously stirred with 25 wt % polycaprolactone diol in DMSO followed by stannous octoate addition. The reaction proceeded for three hours at 80° C. followed by cooling to room temperature. Putrescine was added dropwise with stirring and the reaction was continued at room for 18 hours. PEUU was then precipitated in distilled water, and the wet polymer was subsequently immersed in isopropanol to remove unreacted monomers, and then dried under vacuum at 50° C.

Example 2

Isolation of Extracellular Matrix from Porcine Urinary Bladders (UBM)

Porcine urinary bladders were harvested from pigs immediately following euthanasia. Connective tissue and adipose tissue were removed from the serosal surface and any residual urine was removed by repeated washes with tap water. The tunica serosa, tunica mucosa externa, the tunica submucosa, and most of the tunica muscularis interna were mechanically removed and the luminal urothelial cells of the basement membrane were dissociated by soaking in 1.0 N saline solution yielding a biomaterial composed primarily or exclusively of the basement membrane plus the subjacent tunica propria. This bi-laminate structure was referred to as urinary bladder matrix (UBM). UBM sheets were disinfected for two hours on a shaker in a solution containing 0.1% (v/v) peracetic acid, 4% (v/v) ethanol, and 95.9% (v/v) sterile water. The peracetic acid residue was removed by washing with sterile phosphate-buffered saline (pH=7.4) twice for 15 minutes each and twice for 15 minutes each with sterile water. UBM sheets were subsequently lyophilized and powdered. One gram of lyophilized UBM powder and 100 mg of pepsin were both mixed in 100 mL of 0.01 M HCl. The solution was kept at a constant stir for approximately 48 hours at room temperature (approximately 25° C.). After pepsin digestion, the digest was aliquoted and stored at −20° C. until use or at 4° C. after initial thawing. UBM digest was subsequently lyophilized and re-dissolved in the appropriate electrospinning solvent.

Example 3

Preparation of a UBM Scaffold by Electrospinning

Figures 2A, 2B, 2C, 2D:
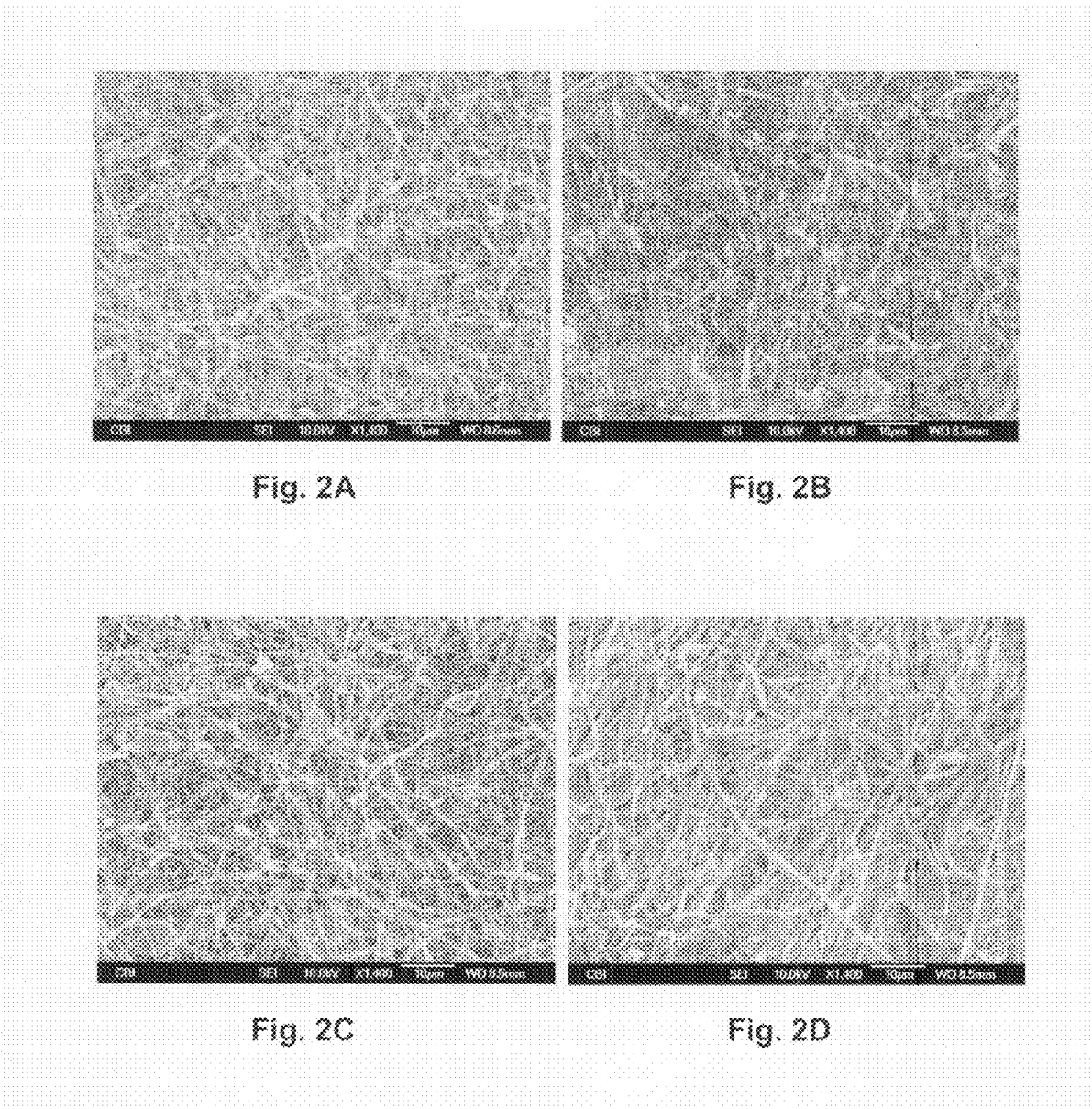
FIGS. 2A-2D are scanning electron micrographs of electrospun urinary bladder matrix (UBM). Morphologies of scaffolds are shown for various wt % of UBM in hexafluoroisopropanol: (A) 9 wt %, (B) 10 wt %, (C) 12 wt %, and (D) 15 wt %. Scale bars are 10 µm.

The urinary bladder matrix (UBM) extract alone was electrospun from hexafluoroisopropanol (HFIP). Several concentrations of UBM were tested and the morphologies of the resulting scaffold were assessed by scanning electron microscopy (FIGS. 2A-2D). The tested concentrations were 6 wt %, 9 wt %, 10 wt %, 12 wt %, and 15 wt % UBM in HFIP. FIG. 2A shows the morphology of the scaffold for electrospun UBM at 9 wt % in HFIP. At concentrations lower than 9 wt %, electrospinning of continuous fibers was not achieved. FIGS. 2B-2D shows the morphology of the scaffold for electrospun UBM at 10 wt % (B), 12 wt % (C), and 15 wt % (D). Electrospinning of fibers was possible at concentrations of 9 wt % and greater. However, agglomerates within the fibers were present at all concentrations.

Example 4

Preparation of a Composite PEUU/UBM Scaffold by Electrospinning

Figure 3:
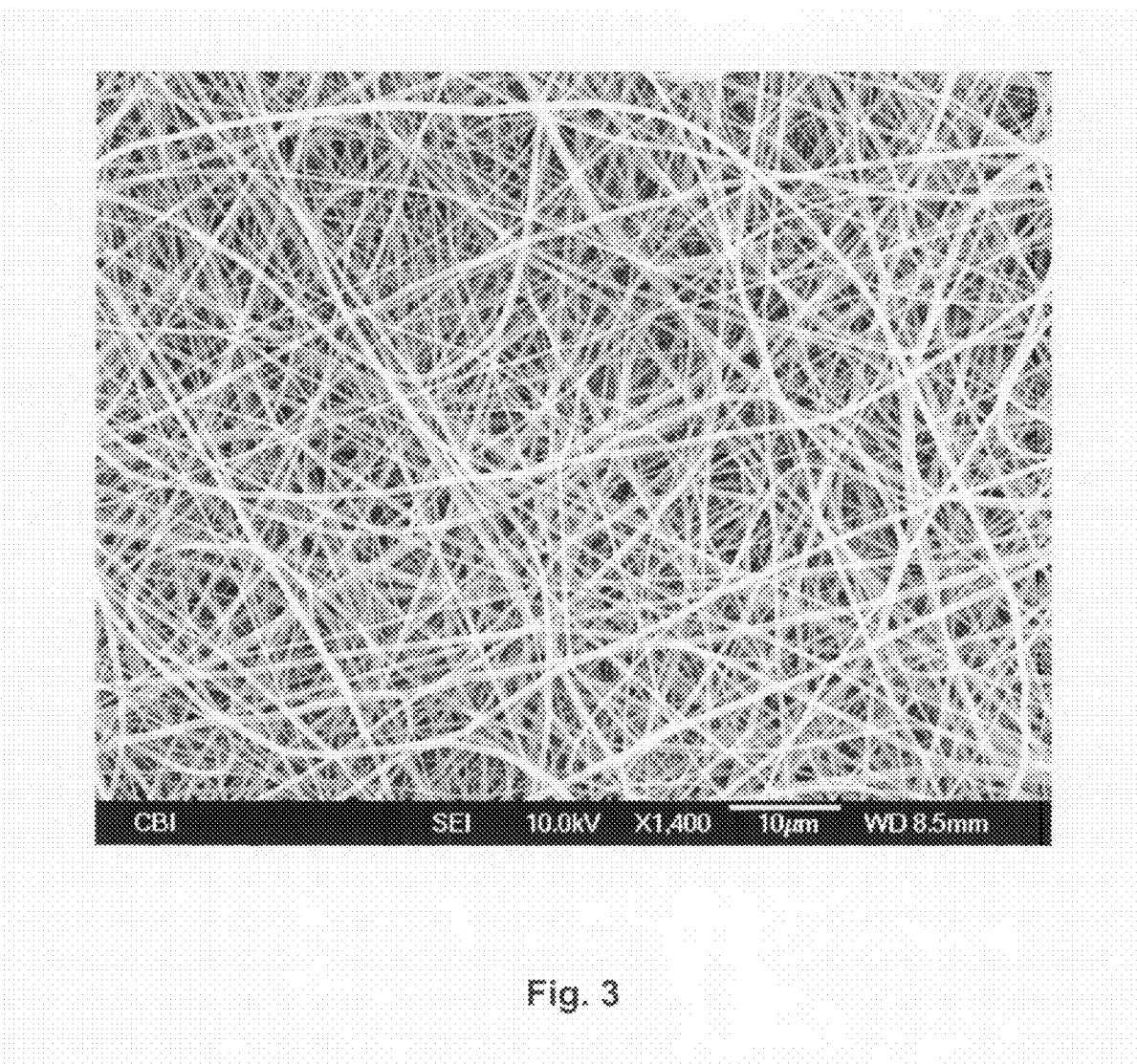
FIG. 3 is a scanning electron micrograph of electrospun PEUU/UBM (50/50) scaffold at 6 wt %. Scale bar is 10 µm.

A composite scaffold containing poly(ester urethane) urea elastomer (PEUU) and urinary bladder matrix (UBM) was made. As the water-soluble electrospun UBM was a fragile and brittle material, it was blended with PEUU before electrospinning to enhance its mechanical properties. PEUU and UBM were mixed at a 1:1 ratio (w/w) and then dissolved at 6 wt % in hexafluoroisopropanol. Continuous artifact free fibers were observed as in FIG. 3. The scaffold was both strong and distensible with a tensile strength of 4.9±1.6 MPa and a breaking strain of 85±28%. The scaffold was also more resistant to degradation compared with electrospun UBM alone.

Figure 4:
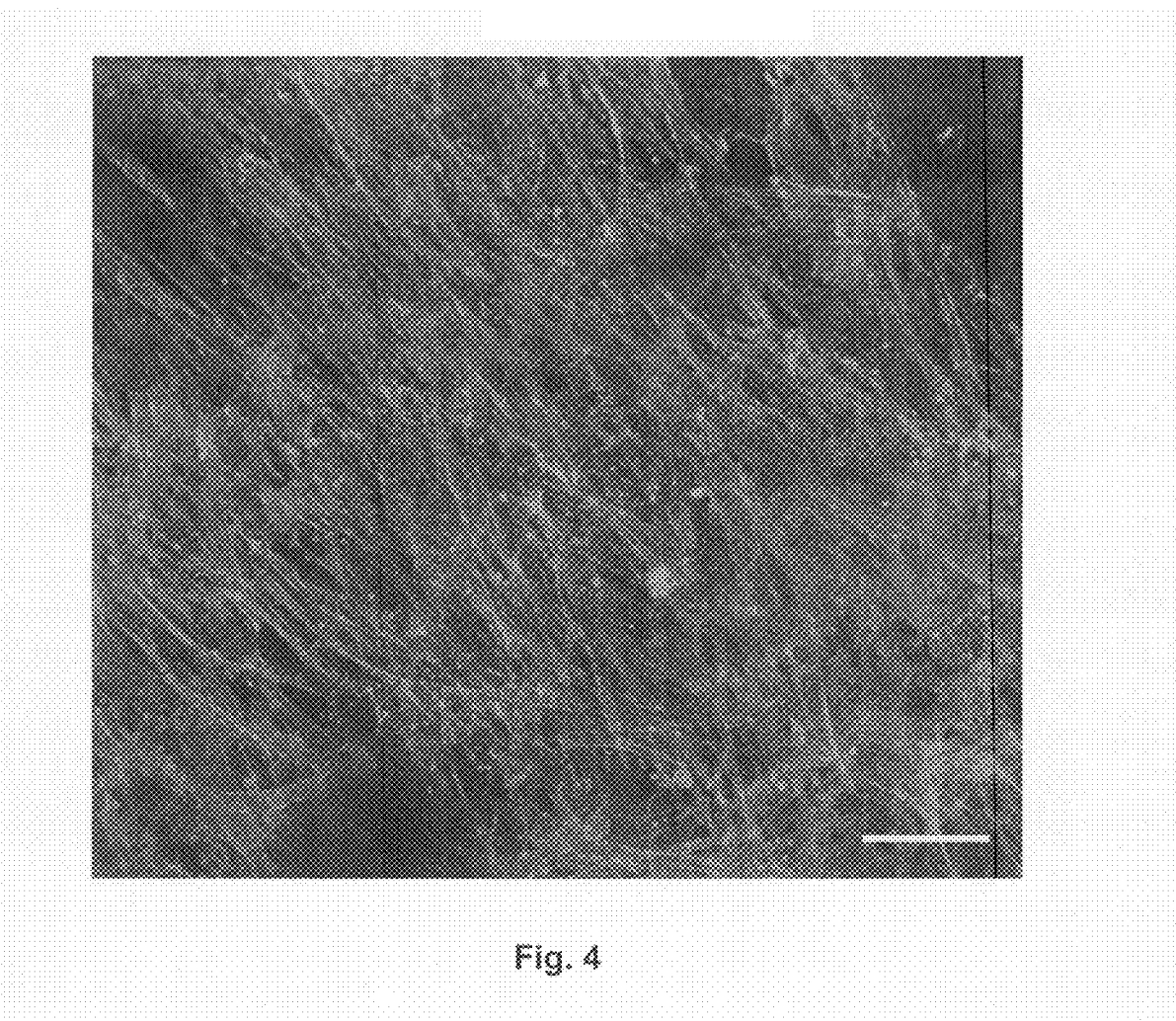
FIG. 4 is a confocal photomicrograph of immunohistochemically-stained smooth muscle cells after being cultured on electrospun PEUU/UBM scaffold for ten days. Stains show f-actin (red) and nuclei (blue). Scale bar is 40 µm.

Smooth muscle cells were cultured on the electrospun PEUU/UBM scaffold for ten days. FIG. 4 shows a confocal photomicrograph of smooth muscle cells cultured on electrospun PEUU/UBM scaffold for ten days. The cells appear spread and healthy near the scaffold surface.

Example 5

Figure 5A:
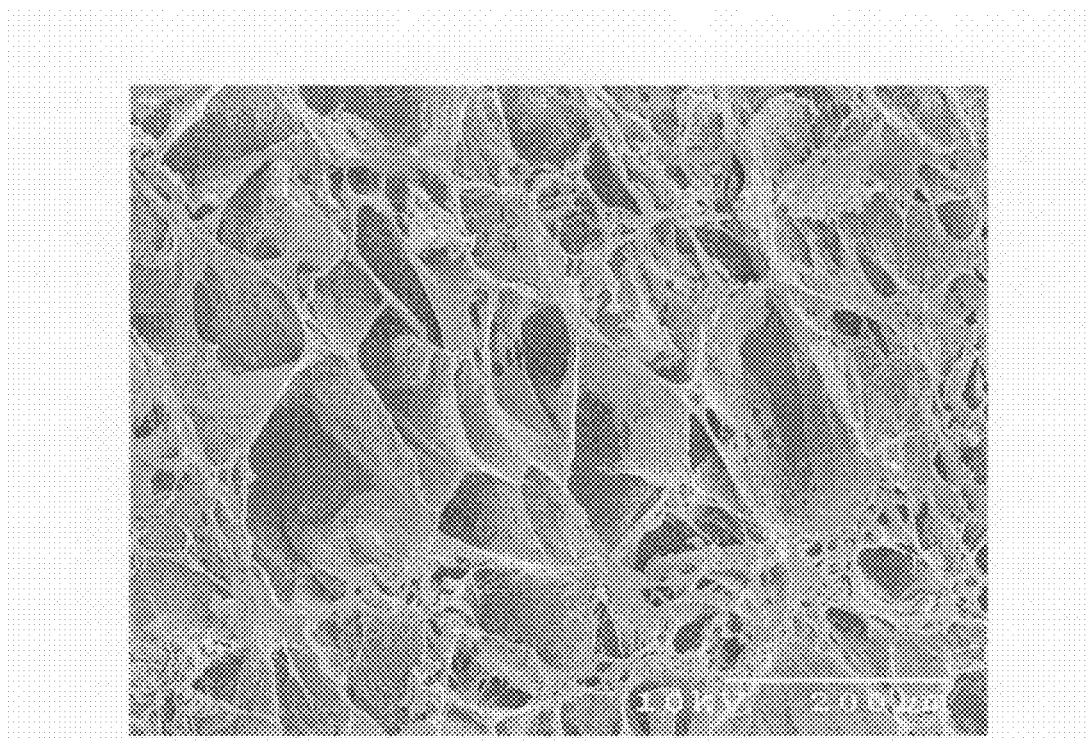
FIG. 5A-5B are scanning electron micrographs of thermally induced phase separation processed PEUU/UBM (90/10) scaffold.
Figure 5B:
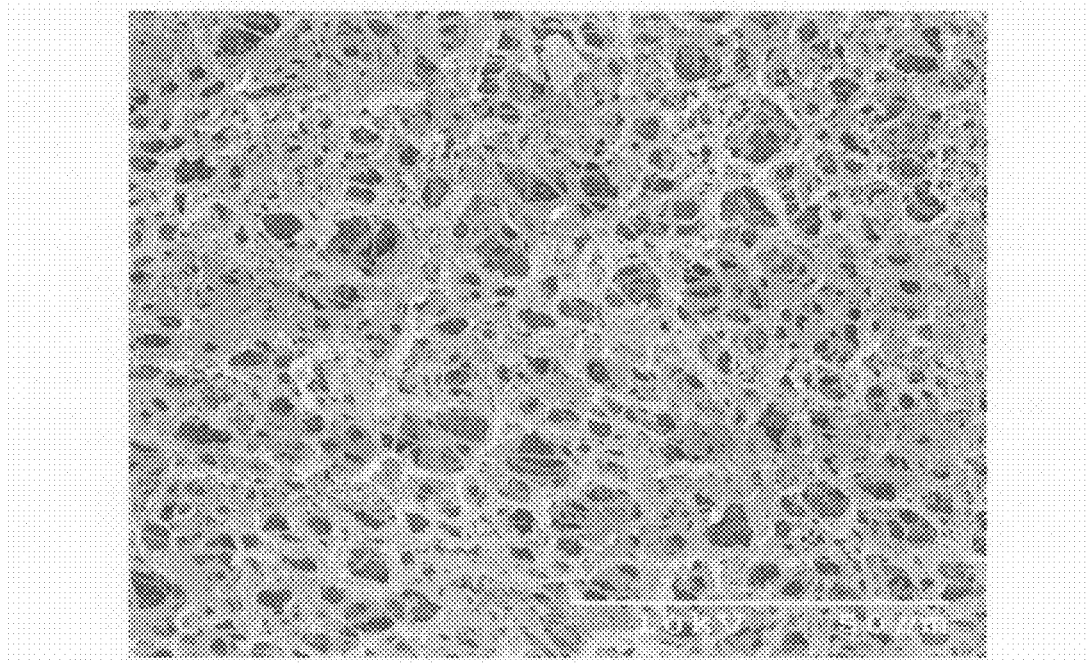

Preparation of a Composite PEUU/UBM Scaffold by Thermally Induced Phase Separation Highly macroporous composite scaffolds were made using thermally induced phase separation (TIPS). PEUU was dissolved in DMSO to form solutions. ECM powder from urinary bladder matrix was uniformly dispersed in DMSO by using a blender at room temperature. This UBM suspension was added into the PEUU solution at 80° C. and dispersed. A mixture with PEUU at a final concentration of 8 wt % and a PEUU/UBM ratio of 90:10 was acquired. The mixture was then injected into a glass cylinder mold fitted with rubber stoppers. The mold was constructed of two glass tubes, the outer diameter of the inner tube was 5 mm, and the inner diameter of outer tube was 10 mm. The mold was cooled to a temperature of −80° C. for 3 hours and was then removed and placed into absolute alcohol at a temperature of 4° C. for 7 days to extract the DMSO. The alcohol was changed daily. The scaffold was then immersed in water and freeze-dried, followed by vacuum dry for 24 hours at room temperature. FIG. 5A shows the surface and FIG. 5B shows the cross-section of a representative TIPS-processed PEUU/UBM (90/10) scaffold. This material was also strong and flexible with a tensile strength of $1.2 \pm 0.2$ MPa and an elongation at break of $201 \pm 16\%$.

Having described this invention, it will be understood to those of ordinary skill in the art that the same can be performed within a wide and equivalent range of conditions, formulations and other parameters without affecting the scope of the invention or any embodiment thereof.

---

We claim:

1. A scaffold comprising a mixture of a synthetic polymer and solubilized extracellular matrix, wherein the scaffold is porous, biodegradable, and biocompatible, and wherein the scaffold is produced by electrospinning the synthetic polymer and the solubilized extracellular matrix to form a scaffold.

2. The scaffold of claim 1, in which the synthetic polymer comprises a thermoplastic biodegradable polymer.

3. The scaffold of claim 2, wherein the thermoplastic biodegradable polymer comprises one or both of a poly(ester urethane) urea elastomer and a poly(ether ester urethane urea) elastomer.

4. The scaffold of claim 3, wherein the polymer comprises a diamine.

5. The scaffold of claim 4, wherein the diamine is putrescine.

6. The scaffold of claim 4, wherein the diamine is lysine ethyl ester.

7. The scaffold of claim 3, wherein the polymer comprises a polycaprolactone.

8. The scaffold of claim 3, wherein the polymer comprises a polycaprolactone diol.

9. The scaffold of claim 3, wherein the polymer comprises a triblock copolymer comprising polycaprolactone.

10. The scaffold of claim 9, wherein the polymer comprises a polycaprolactone-b-polyethylene glycol-b-polycaprolactone triblock copolymer.

11. The scaffold of claim 3, wherein the polymer is functionalized with an adhesion-promoting peptide.

12. The scaffold of claim 11, wherein the adhesion-promoting peptide comprises the oligopeptide RGD.

13. The scaffold of claim 3, wherein the polymer comprises an isocyanate derivative, a polycaprolactone diol, and a diamine chain extender.

14. The scaffold of claim 13, wherein the ratio of isocyanate derivative:polycaprolactone diol:diamine chain extender is 2:1:1.

15. The scaffold of claim 3, wherein the polymer comprises an isocyanate derivative, a triblock copolymer comprising polycaprolactone, and a diamine chain extender.

16. The scaffold of claim 15, wherein the ratio of isocyanate derivative:triblock copolymer:diamine chain extender is 2:1:1.

17. The scaffold of claim 1, wherein the solubilized extracellular matrix is isolated from urinary bladder tissue.

18. The scaffold of claim 17, wherein the solubilized extracellular matrix comprises epithelial basement membrane and subjacent tunica propria.

19. The scaffold of claim 17, wherein the solubilized extracellular matrix-comprises tunica submucosa.

20. The scaffold of claim 17, wherein the solubilized extracellular matrix comprises epithelial basement membrane, subjacent tunica propria and tunica submucosa.

21. The scaffold of claim 1, wherein the solubilized extracellular matrix is isolated from small intestinal submucosa or the dermis of the skin.

22. The scaffold of claim 1, comprising a therapeutic agent.

23. The scaffold of claim 22, wherein the therapeutic agent is an antimicrobial agent chosen from one or more of: isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate.

24. The scaffold of claim 22, wherein the therapeutic agent is a growth factor chosen from one or more of: basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins, and interferons.

25. The scaffold of claim 22, wherein the therapeutic agent is in the form of cells.

26. The scaffold of claim 25, wherein the cells are one or more of stem cells, precursor stem cells, smooth muscle cells, skeletal myoblasts, myocardial cells, endothelial cells, and genetically modified cells.

27. The scaffold of claim 1, wherein the scaffold is produced by suspending a synthetic polymer and solubilized extracellular matrix in a solvent to form a mixture; and electrospinning the mixture to form a scaffold.

28. The scaffold of claim 1, wherein the scaffold is produced by suspending a synthetic polymeric component in a solvent to form a solution, suspending solubilized extracellular matrix in another solvent to form a solution; and independently electrospinning the solutions to form a scaffold.

29. The scaffold of claim 1 in which the scaffold is elastomeric.

30. A method of producing a medical device comprising a scaffold comprising forming a porous, biodegradable, and biocompatible scaffold from a synthetic polymer and solubilized extracellular matrix, wherein the scaffold is produced by electrospinning the synthetic polymer and the solubilized extracellular matrix to form a scaffold.

31. The method of claim 30, comprising forming a scaffold by electrospinning the synthetic polymer and the solubilized extracellular matrix to form a scaffold on a target on the medical device.

32. The method of claim 30, in which the scaffold is produced by suspending a synthetic polymer in a solvent to form a solution, suspending solubilized extracellular matrix in another solvent to form a solution; and independently electro spinning the solutions together to form a scaffold.

33. A method of promoting wound healing or tissue generation or regeneration in a patient comprising implanting the scaffold of claim 1 at or near a site for wound healing or tissue generation or regeneration in the patient.

34. A method of promoting wound healing or tissue generation or regeneration in a patient, comprising
   a) contacting the scaffold of claim 1 with cells in vitro;
   b) culturing the cells in vitro so that the cells grow in and/or on the scaffold;
   c) implanting the scaffold at or near a site for wound healing or tissue generation or regeneration in the patient.

35. The method of claim 34, wherein the scaffold comprises a therapeutic agent.

36. The method of claim 35, wherein the therapeutic agent is an antimicrobial agent chosen from one or more of isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate.

37. The method of claim 35, wherein the therapeutic agent is a growth factor chosen from one or more of basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins, and interferons.

38. The method of claim 34, the scaffold comprises a therapeutic agent.

39. The method of claim 38, wherein the therapeutic agent is an antimicrobial agent chosen from one or more of isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate.

40. The method of claim 38, wherein the therapeutic agent is a growth factor chosen from one or more of basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins, and interferons.

* * * * *

UNITED STATES PATENT AND TRADEMARK OFFICE
CERTIFICATE OF CORRECTION

PATENT NO. : 8,535,719 B2  
APPLICATION NO. : 11/825540  
DATED : September 17, 2013  
INVENTOR(S) : Stephen F. Badylak et al.

Page 1 of 1

It is certified that error appears in the above-identified patent and that said Letters Patent is hereby corrected as shown below:

Title Page 2, Column 1, Item (56) References Cited, Line 45, delete "Biaixal" and insert -- Biaxial --

Title Page 2, Column 2, Item (56), Line 20, delete "immobiliation" and insert -- immobilization --

Signed and Sealed this
Fourth Day of February, 2014

Michelle K. Lee
*Deputy Director of the United States Patent and Trademark Office*

SEQUENCE LISTING

```
<160> NUMBER OF SEQ ID NOS: 7

<210> SEQ ID NO 1
<211> LENGTH: 4
<212> TYPE: PRT
<213> ORGANISM: Homo sapiens

<400> SEQUENCE: 1

Arg Gly Asp Ser
1

<210> SEQ ID NO 2
<211> LENGTH: 4
<212> TYPE: PRT
<213> ORGANISM: Homo sapiens

<400> SEQUENCE: 2

Arg Glu Asp Val
1

<210> SEQ ID NO 3
<211> LENGTH: 5
<212> TYPE: PRT
<213> ORGANISM: Homo sapiens

<400> SEQUENCE: 3

Pro His Ser Arg Asn
1               5

<210> SEQ ID NO 4
<211> LENGTH: 5
<212> TYPE: PRT
<213> ORGANISM: Homo sapiens

<400> SEQUENCE: 4

Lys Asn Glu Glu Asp
1               5

<210> SEQ ID NO 5
<211> LENGTH: 5
<212> TYPE: PRT
<213> ORGANISM: Homo sapiens

<400> SEQUENCE: 5

Tyr Ile Gly Ser Arg
1               5
```

```
<210> SEQ ID NO 6
<211> LENGTH: 5
<212> TYPE: PRT
<213> ORGANISM: Homo sapiens

<400> SEQUENCE: 6

Ile Lys Val Ala Val
1               5

<210> SEQ ID NO 7
<211> LENGTH: 4
<212> TYPE: PRT
<213> ORGANISM: Homo sapiens

<400> SEQUENCE: 7

Asp Gly Glu Ala
1
```